(12) United States Patent
McCartan et al.

(10) Patent No.: US 7,266,987 B2
(45) Date of Patent: Sep. 11, 2007

(54) ULTRASOUND TRANSMIT AND RECEIVE PATH CALIBRATION METHODS AND SYSTEMS

(75) Inventors: Dermot P. McCartan, Mountain View, CA (US); John D. Marshall, Campbell, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/376,938

(22) Filed: Mar. 15, 2006

(65) Prior Publication Data

US 2006/0191315 A1    Aug. 31, 2006

Related U.S. Application Data

(62) Division of application No. 10/812,335, filed on Mar. 29, 2004, now Pat. No. 7,162,912.

(51) Int. Cl.
*G01N 29/30* (2006.01)

(52) U.S. Cl. ............................................. 73/1.82
(58) Field of Classification Search .......... 73/1.82; 367/13
See application file for complete search history.

(56) References Cited

U.S. PATENT DOCUMENTS

| | | | |
|---|---|---|---|
| 3,202,968 A | 8/1965 | Eady, Jr. et al. ........... 367/13 X |
| 3,351,898 A | 11/1967 | Romberg ..................... 367/13 |
| 3,631,450 A | 12/1971 | Chalfant ..................... 340/328 |
| 3,789,352 A | 1/1974 | Forsyth ........................ 367/13 |
| 4,003,018 A | 1/1977 | McCormick ............. 367/13 X |
| 4,043,180 A | 8/1977 | Morris et al. ............ 73/1.82 X |
| 4,972,379 A | 11/1990 | Harris, Jr. ..................... 367/13 |
| 5,075,694 A * | 12/1991 | Donnangelo et al. ....... 342/455 |
| 5,095,464 A | 3/1992 | Bednar ......................... 367/13 |
| 5,159,576 A | 10/1992 | Forster et al. ................ 367/13 |
| 5,267,219 A * | 11/1993 | Woodward .................... 367/99 |
| 5,477,504 A | 12/1995 | Hagerty ....................... 367/13 |
| 5,542,452 A | 8/1996 | Carver, Jr. et al. |
| 5,675,554 A | 10/1997 | Cole et al. |
| 5,866,796 A | 2/1999 | Chia et al. ................... 73/1.82 |
| 5,995,348 A | 11/1999 | McCartan et al. |
| 6,208,189 B1 | 3/2001 | Freeman et al. |
| 6,238,344 B1 | 5/2001 | Gamelsky et al. |
| 6,270,460 B1 | 8/2001 | McCartan et al. |
| 6,575,906 B1 | 6/2003 | Schembri, Jr. et al. |
| 6,671,222 B2 | 12/2003 | Wilson et al. ................ 367/13 |
| 2004/0004905 A1 | 1/2004 | Lyon et al. ................... 367/13 |

FOREIGN PATENT DOCUMENTS

| | | | |
|---|---|---|---|
| EP | 393828 B1 | 10/1993 | |
| EP | 249871 B1 | 4/1995 | |
| JP | 54149669 A | 11/1979 | ................... 367/13 |
| JP | 62064972 A | 3/1987 | ................... 367/13 |
| JP | 02300685 A | 12/1990 | ................... 367/13 |
| JP | 03122586 A | 5/1991 | ................... 367/13 |
| JP | 04344486 A | 12/1992 | ................... 367/13 |

* cited by examiner

*Primary Examiner*—Thomas P. Noland

(57) ABSTRACT

The clipping diodes used to limit voltage during medical diagnostic ultrasound imaging operation are used during calibration operation for measuring amplitude and phase differences. The amplitude and phase measurements using clipping diodes as the calibration node may operate at any frequency, including frequencies less than 20 megahertz as well as frequencies above 20 megahertz. By using the diodes already present, a smaller or more compact calibration system may be provided. More simplistic integration may also result.

9 Claims, 3 Drawing Sheets

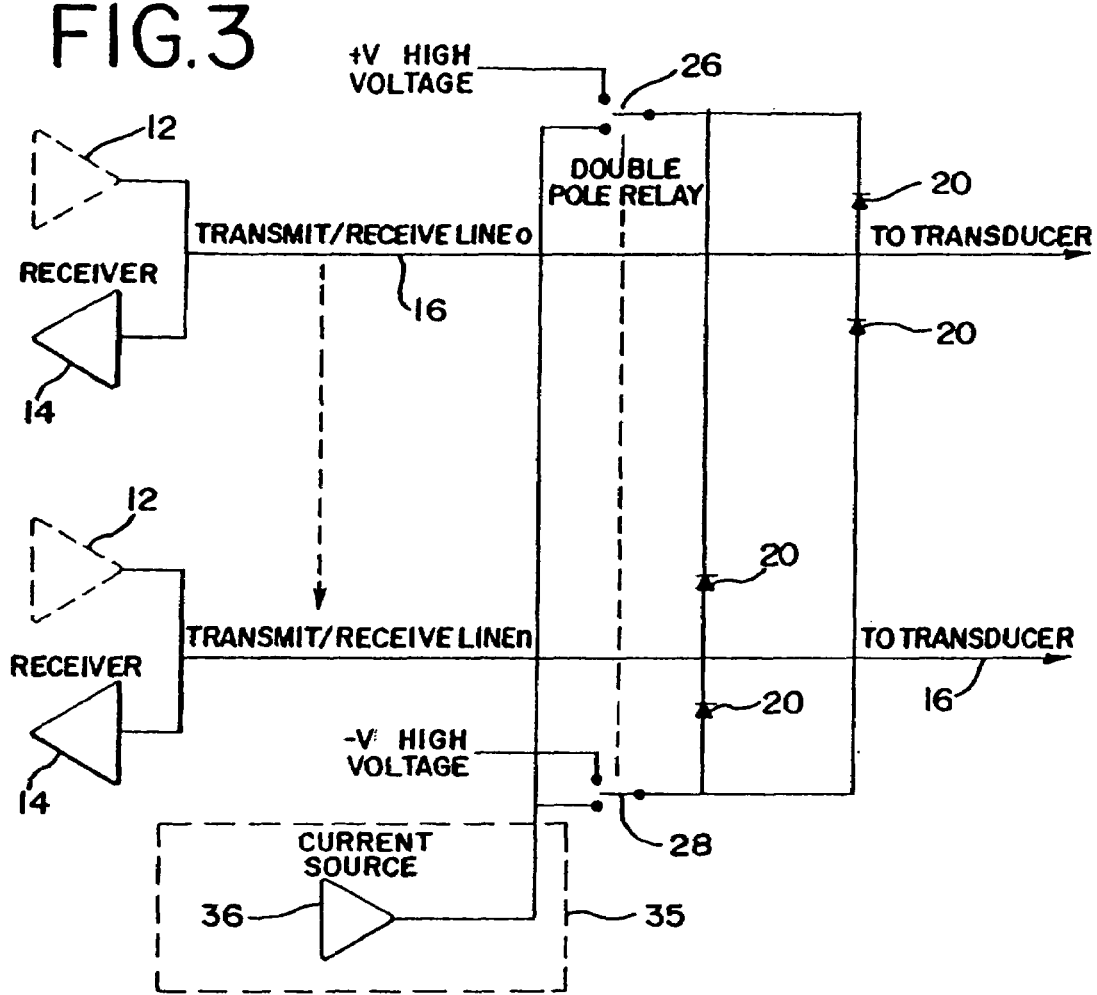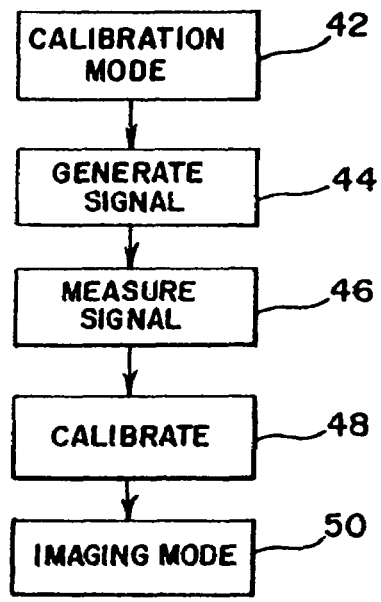

ULTRASOUND TRANSMIT AND RECEIVE PATH CALIBRATION METHODS AND SYSTEMS

CROSS-REFERENCE TO RELATED APPLICATION

This application is a divisional of U.S. patent application Ser. No. 10/812,335, filed Mar. 29, 2004, now U.S. Pat. No. 7,162,912.

BACKGROUND

The present invention relates to calibrating transmitters and receivers of an ultrasound imaging system. In particular, amplitude and phase adjustments for one channel relative to other channels are provided by calibration.

By measuring amplitude and/or phase differences between different channels of an ultrasound imaging system, system induced differences or artifacts may be minimized. For example, transmit wave forms of one channel are increased in amplitude, decreased in amplitude, or phase rotated to account for system induced differences relative to another channel. Likewise, receive performance may also be calibrated. Calibration may allow for images with less system induced noise. Calibration ascertains output amplitude and phase shifts between transmitters, or ascertains voltage gain and phase shift between receivers.

Hardware is positioned within the imaging system adjacent to a transducer port for calibration. The coupling node for calibration is used to inject signals of well-defined properties for receiver calibration and precisely monitor signals for transmit calibration. FIG. 1 shows one embodiment of a calibration system 10 for ultrasound imaging. A plurality of transmitters 12 and receivers 14 connect with respective transmit and receive lines 16. For use in imaging, pairs of diodes 20 connect to respective transmit and receive lines 16. One diode 20 of each pair connects with a positive high voltage source, and the other diode 20 of each pair connects with a negative high voltage source. The positive and negative voltage sources act to limit a possible voltage output on each transmit and receive line to avoid injury.

A calibration node 18 also connects with each of the transmit and receive lines 16. The calibration node 18 is used for calibrating prior to imaging. The calibration node 18 includes resistive or capacitive components. For example, each transmit and receive line 16 is connected together through low valued capacitors (e.g., less then 50 picofarads) to a common node or conductor. For example, a printed wiring board trace is run under the transmit and receive lines to form the capacitive common node. The common node is connected to ground through a larger capacitor (e.g., greater than 1,000 picofarads) in order to limit the amount of unwanted crosstalk introduced from line-to-line capacitance. For calibrating receivers, a signal is generated on the common node, and each transmit and receive lines 16 is measured sequentially using the receivers 14. Amplitude and phase differences are identified from the measured signal. For transmit calibration, the transmitters 12 sequentially generate transmit waveforms on the transmit and receive line 16, and an amplitude and phase is measured at the common node. However, this capacitive calibration node may not be suitable for systems operating at high frequencies, such as greater than 20 MHz. As the frequency increases, the impedance of a capacitor decreases. The capacitive impedance to ground decreases within the calibration node 18, which may cause discontinuity in the transmission lines, likely degrading system performance.

In another approach, the calibration node 18 is a resistive device. Each of the transmit and receive lines 16 are connected together through resistors, such as on the order of less than 1 kilo-ohms. The common node is then connected to ground through a relatively small valued resistor, such as less than 100 ohms, in order to limit the amount of unwanted crosstalk introduced from line-to-line resistance. The common node is used as discussed above to determine relative amplitude and phases for both transmit and receive operation. In normal imaging operation, the resistive based calibration node 18 may operate over a wide range of frequency signals, including greater than 20 megahertz. However, in calibration mode, as the frequency increases, the resistors increasingly act as low pass filters because of stray capacitance to ground. Degraded calibration performance may result. Substantial transmit power loss over all frequencies may also result.

BRIEF SUMMARY

By way of introduction, the preferred embodiments described below include methods and systems for calibration of an ultrasound transmitter and/or receiver. The clipping diodes used to limit voltage during imaging operation may be used during calibration operation for measuring amplitude and phase differences. Using clipping diodes as the calibration node may allow operation at any frequency, including frequencies less than 20 megahertz as well as frequencies above 20 megahertz. By using the diodes already present for imaging reasons, a smaller or more compact calibration system may be provided. More simplistic integration may also result.

In a first aspect, a system for calibration of an ultrasound transmitter and/or receiver is provided. A clipping diode connects with an ultrasound transmit, receive or transmit/receive path. A voltage source is connectable with the clipping diode. A switch is between the clipping diode and the first voltage source for selecting between calibration and normal modes of operation.

In a second aspect, a system for calibration of an ultrasound transmitter and receiver is provided. Pairs of clipping diodes connect with respective ones of transmit/receive ultrasound paths. A positive voltage source connects with one of each pair of the clipping diodes, and a negative voltage source connects with another of each pair of the clipping diodes. A switch is provided between the first ones of the clipping diodes and the positive voltage source. Another switch is connected between the second ones of the clipping diodes and a negative voltage source. The switches are operable to select between calibration and imaging modes of operation.

In a third aspect, a method is provided for calibration of an ultrasound transmitter and/or receiver. At least one of phase and amplitude are measured with a signal provided through a clipping diode. The ultrasound transmitter and/or receiver are calibrated as a function of the phase or amplitude information.

In a fourth aspect, an improvement in a method for calibrating a transmit/receive path of an ultrasound system where clipping diodes limit an output voltage of the transmit/receive path is provided. The improvement includes using the clipping diodes as a calibration node for the transmit/receive path.

The present invention is defined by the following claims, and nothing in this section should be taken as a limitation on those claims. Further aspects and advantages of the invention are discussed below in the Detailed Description of the Drawings and Presently Preferred Embodiments. The aspects and advantages discussed within this Summary as well as the further aspects and advantages may be now claimed or later claimed.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 is a circuit diagram of one embodiment of an ultrasound receiver calibration system using clipping diodes;

FIG. 4 is a flow chart diagram of one embodiment of a method for calibrating an ultrasound system.

DETAILED DESCRIPTION OF THE DRAWINGS AND PRESENTLY PREFERRED EMBODIMENTS

For safety reasons, transmit lines or transmit/receive lines in ultrasound medical diagnostic imaging systems are connected to positive and negative high voltage sources with clipping diodes. In the event of a system fault, the clipping diodes ensure that the output voltage may not exceed safety limits. The same clipping diodes may be used for calibration. In imaging operation, the clipping diodes are connected to the high voltage sources. For calibration operation, the clipping diodes are connected to a signal source or the calibration receiver. Using the common connection of the clipping diodes as a calibration node may reduce cost and board area since capacitors and resistors of a capacitive or resistive calibration node may be eliminated. During imaging operation, the calibration node may not introduce a discontinuity in the transmission lines, allowing for higher frequency operation.

Figure 1:
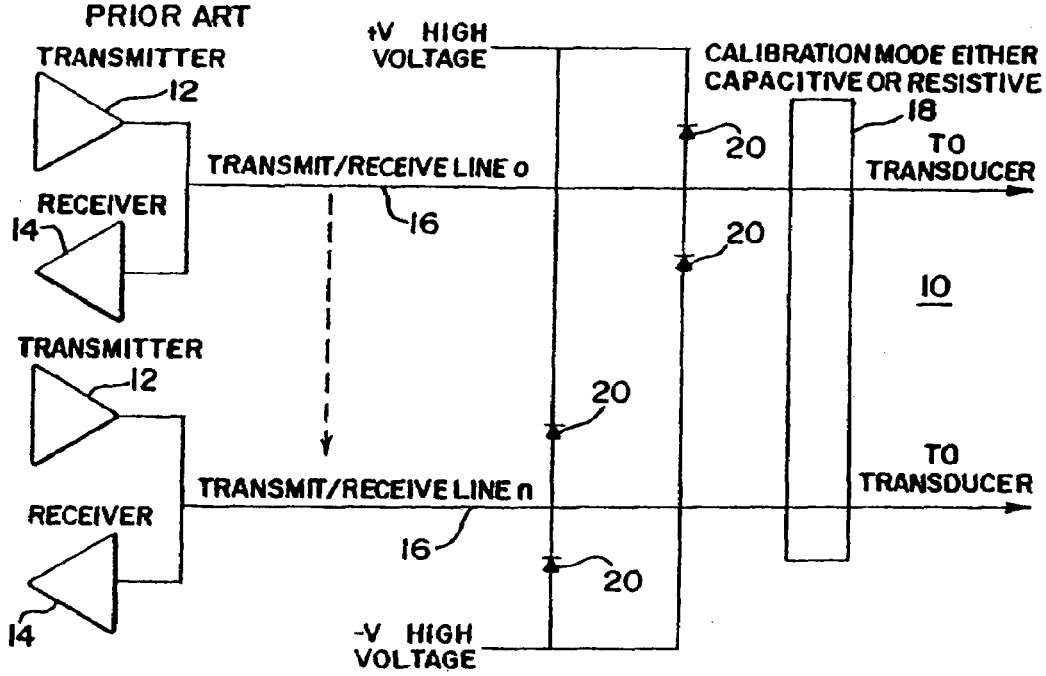
FIG. 1 is a circuit diagram of a prior art calibration system for ultrasound transmitters and receivers.
Figure 2:
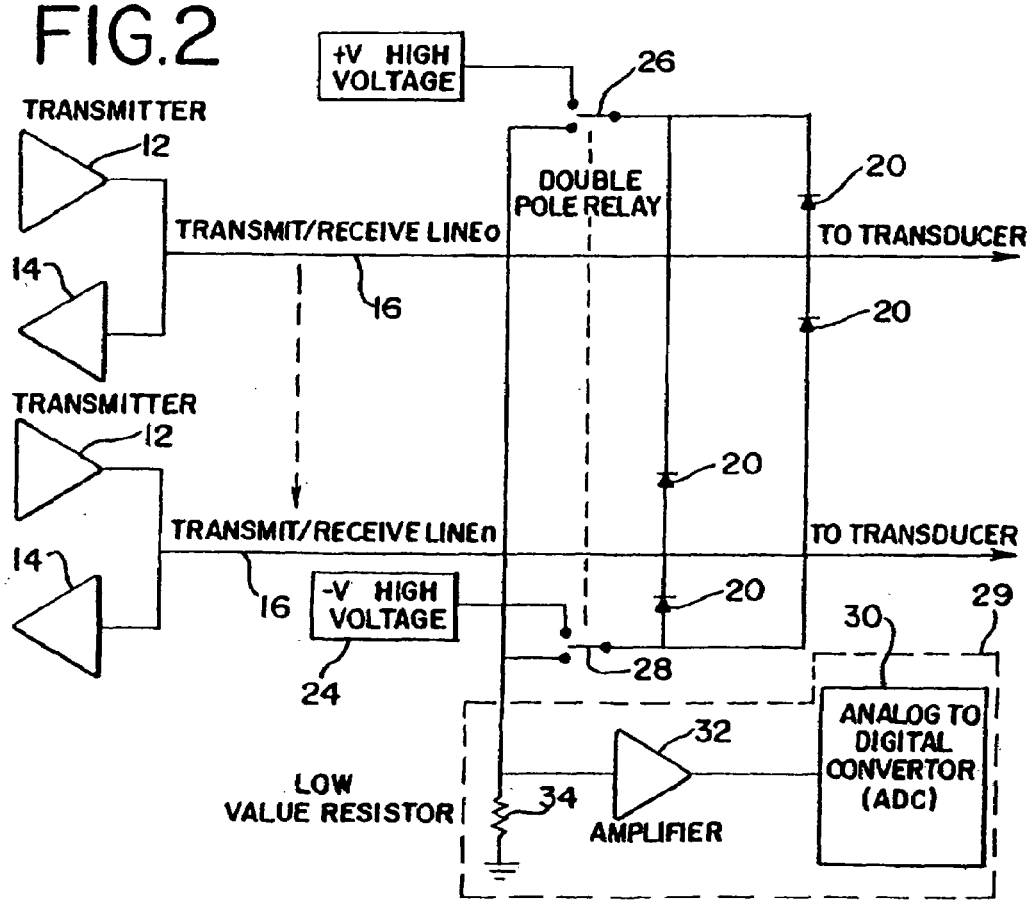
FIG. 2 is a circuit diagram showing one embodiment of an ultrasound transmitter calibration system using clipping diodes.
Figure 5:
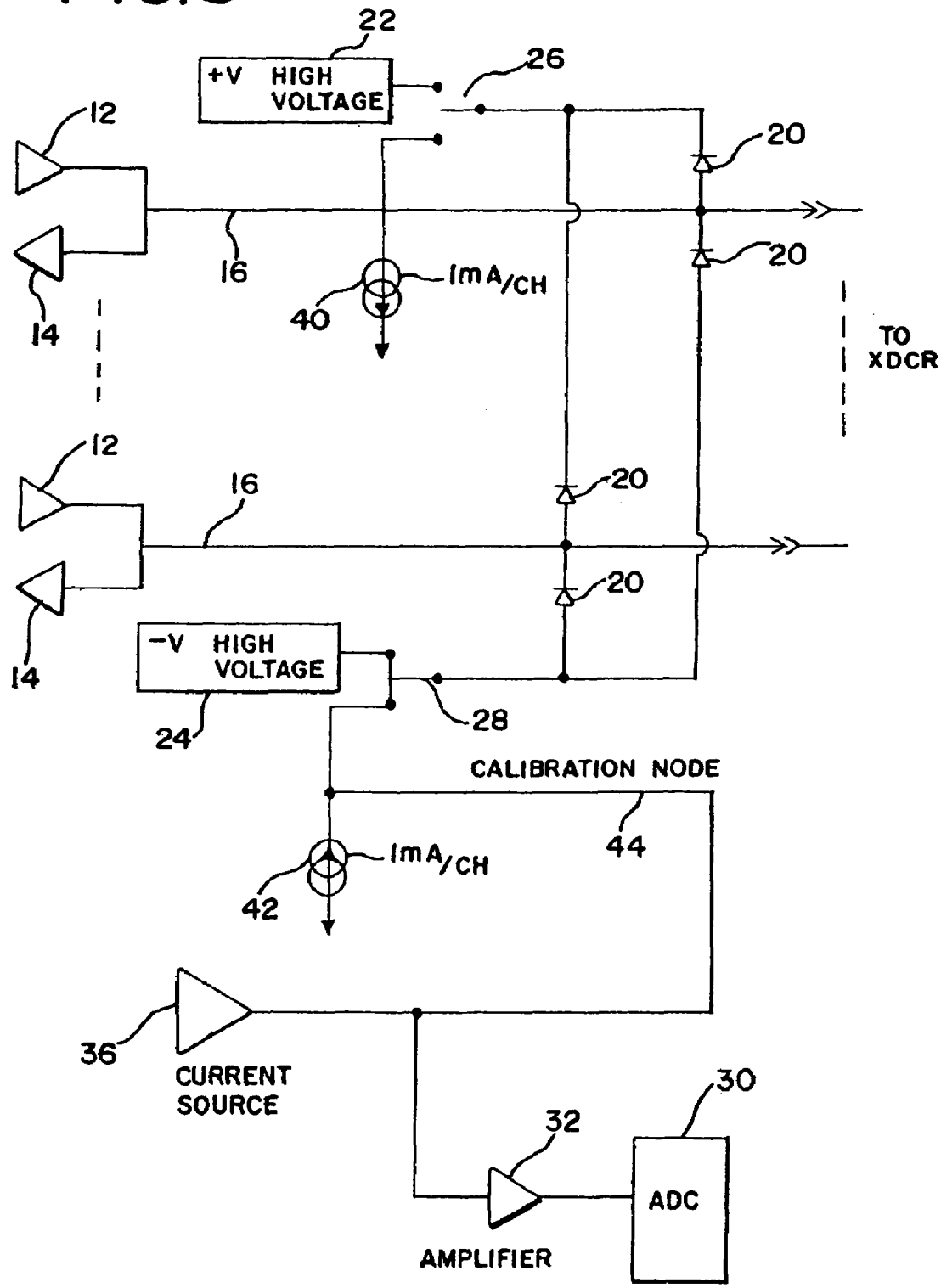
FIG. 5 is a circuit diagram showing one embodiment of a transmitter and receiver calibration system using clipping diodes.

FIG. 2 shows a system for calibration of an ultrasound transmitter in one embodiment. FIG. 3 shows a system for calibration of an ultrasound receiver in one embodiment. While shown separately, the systems may be combined to provide a system for calibration of ultrasound transmitters and receivers as shown in FIG. 5. The combination is provided by connecting the current source 36 to the input of the amplifier 32 and operating the current source 36 and the amplifier 32 at different times. Alternatively, a switch or other device is provided to switch between calibration of the transmitters and its associated structure and calibration of the receiver and its associated structure. As yet another alternative, the switches 26 and 28 are three-pole switches for switching between the imaging operation, transmit calibration and receive calibration.

The systems of FIGS. 2 and 3 include transmitters 12, receivers 14, transmit/receive lines 16, clipping diodes 20, a positive high voltage source 22, a negative high voltage source 24, and switches 26, 28. Additional, different and fewer components may be provided, such as providing transmit lines 16 with transmitters without a receiver 14. As another example, the receiver 14 is provided with a receive line 16 without the transmitter 12. As yet another example, a multiplexer or partial beamforming for combining data from a plurality of transducer elements onto a single transmit or receive line 16 is provided.

The transmitter 12 is an amplifier, analog-to-digital converter, switches, transistors, filters, delays, waveform generator or other now known or later developed device for generating unipolar, bipolar or sinusoidal waveforms, such as a transmit beamformer channel. For example, the transmitter 12 is a transistor network for generating unipolar or bipolar square waves. Alternatively, the transmitter 12 is a memory, phase rotators, filters, amplifiers and other structures disclosed in U.S. Pat. No. 5,675,554, the disclosure of which is incorporated herein by reference, for generating sinusoidal waveforms.

The receiver 14 is a filter, delay, phase rotator, mixer, summer, amplifier or other now known or later developed ultrasound receiver, such as an ultrasound receive beamformer channel. The receiver 14 connects with the transmitter 12 through a transmit/receive switch connected to the transmit/receive lines 16. Alternatively, other forms of protecting the receiver 14 from the output of the transmitter 12 are provided.

The transmit/receive lines 16 are conductive lines, such as traces on a circuit board, a flexible circuit, a bus, coaxial cables, or other conductive structures now known or later developed. Each of the transmit/receive lines 16 operates as separate ultrasound path. For phased array beamforming, a plurality of the transmit/receive line 16 are used for focusing along one or more scan lines in connection with a respective plurality of transducer elements. For transmission, the transmit/receive lines 16 acts as a transmit path from the transmitter 12 to an associated transducer element. For receive operations, the transmit/receive line 16 operates as a receive path from the transducer element to the associated receiver 14. In alternative embodiments, separate transmit and receive paths are provided. None or one or more intervening components may be provided along the transmit/receive line 16, such as a preamplifier, multiplexer, transmit/receive switch, filter or other structures. In one embodiment, the transmit/receive line 16 is a path between an amplifier and the transducer, such as between an apodization amplifier of the transmitter 12 or an apodization amplifier or preamplifier of the receiver 14 and an associated transducer element.

A pair of clipping diodes 20 connects with each of the transmit/receive lines 16. The clipping diodes 20 are zener diodes, transistor based diodes or any now known or later developed diodes. One diode 20 is connected with the transmit/receive line 16 to prevent current from passing until a voltage on the transmit/receive line reaches a high positive voltage. Conversely, another of the pair of diodes 20 is connected to the transmit/receive line 16 to prevent the flow of current through the diode 20 until the voltage on the transmit/receive line 16 drops to a high negative voltage. The pairs of clipping diodes 20 for the transmit/receive lines 16 are connected together in parallel as shown in FIGS. 2 and 3. Additional, different or fewer diodes 20 may be used. During imaging operation, the pairs of diodes 20 connected with respective ones of the transmit/receive lines 16 act as clipping diodes to prevent a voltage on the transmit/receive line from exceeding the high positive voltage or high negative voltage.

The high positive voltage and high negative voltage are set by the positive high voltage source 22 and the negative high voltage source 24. In one embodiment, the high voltage sources are 200 and −200 volts, but other voltage values may be used. The high voltage sources 22, 24 are transformers, voltage dividers or other now known or later developed voltage sources. In one embodiment, each of the voltage sources 22, 24 is a DC voltage source, but an AC component may be provided. Each of the voltage sources 22, 24 is connectable with one or more of the clipping diodes 20. For example, the positive high voltage source 22 connects with one of each pair of clipping diodes 20, and the negative high voltage source 24 connects with the other of the clipping diodes 20 of each pair.

The switches 26 and 28 are relays, transistors or other now known or later developed switching devices. Each switch 26, 28 is between one or more clipping diodes 20 and one of the voltage sources 22, 24. For example, the switch 26 is positioned between the high voltage source 22 and half of the clipping diodes 20 or one clipping diode 20 for each transmit/receive line 16. The switch 28 is positioned between the negative high voltage source 24 and the other half of the clipping diodes 20 or one clipping diode 20 for each transmit/receive line 16. In the configurations shown in FIGS. 2 and 3, the switches 26, 28 are double pole relay switches for selecting between an imaging mode of operation through connection to the voltage sources 22 and 24 and a calibration mode of operation by connection to either of the transmit or receive calibration circuitry. In alternative embodiments, a triple pole relay or other switch is provided for selecting between imaging operation, receive calibration and transmit calibration. Additional poles or additional switches may be provided for implementing other functions or selectable connection of other circuitry.

During imaging operation, the switch 26 connects the positive voltage clipping diodes 20 to the positive high voltage source 22. The switch 28 connects the negative clipping diodes 20 to the negative high voltage source 24. Where a fault or other error occurs resulting in a voltage on one or more of the transmit/receive lines, any current and associated voltage in excess of the negative or positive high voltages is drained to the voltage source. As a result, the clipping diodes 20 act to limit the voltage on the transmit/receive line 16 to prevent injury to a user or a patient.

For calibration, the switches 26 and 28 connect the clipping diodes 20 to the transmit calibration circuit 29 and receive calibration circuit 35 or both the transmit and receive calibration circuits 29, 35. The transmit calibration circuit 29 includes an analog-to-digital converter 30, an amplifier 32 and a resistor 34. Additional, different or fewer components may be provided. For example, an analog-to-digital converter 30 is provided without the amplifier 32. Other devices now known or later developed for measuring an amplitude or phase of a signal may be used as the transmit calibration circuit 29.

In one embodiment, the resistor is a 0.33 ohm resistor, but other value resistors may be used depending on the components. For example, the transmitters 12 are operable to provide one to two amps of current. During calibration, all of the transmitters or only one of the transmitters 12 is connected to a single point or calibration node. In the calibration mode, the clipping diodes 20 act as anti-parallel diodes to the calibration node. The calibration node connects with the transmit calibration circuit 29 and is provided through the clipping diodes 20. Each transmitter 12 is sequentially excited to produce a transmit waveform. For a maximum of one to two amps, about a 0.66 positive or negative voltage is generated across a 0.33 ohm resistor.

The amplifier 32 is a feedback amplifier, differential amplifier, transistors or any other now known or later developed amplifier for scaling or increasing the value of the voltage at the resistor 34. The input of the amplifier 32 connects with each of the switches 26 and 28 when closed for calibration mode operation and with the resistor 34. The resistor 34 connects the input of the amplifier 32 to ground, such as a relative or absolute ground.

The analog-to-digital converter 30 is a digital circuit, analog circuit, combinations thereof or any other now known or later developed analog-to-digital converter. The analog-to-digital converter 30 connects with the switches 26 and 28 through the amplifier 32. In response to the output of the amplifier 32, the analog-to-digital converter 30 generates digital values representing the analog waveform received from a transmitter 12 through the calibration node for calibration. A microprocessor or other circuit is then used to identify a maximum amplitude, peak positive amplitude, peak negative amplitude and/or relative phasing. By comparing the amplitudes and phase information for each of the transmitters 12, a relative phase and/or amplitude adjustment of one transmitter 12 to other transmitters 12 is determined. The relative adjustment is implemented in the amplifiers and delays or phase rotators of the transmitter 12 so that more uniform transmit waveforms are generated by each of the transmitters 12.

Referring to FIG. 3, the receive calibration circuit 35 includes a current source 36. Additional or different components may be provided. The current source 36 is a transistor, amplifier, integrated circuit, operational amplifier, passive components, combinations thereof or other now known or later developed current source 36. The current source 36 connects with the calibration node through the switches 26 and 28. Using the switches 26 and 28, the clipping diodes 20 act as anti-parallel diodes. In alternative embodiments, one of the switches 26, 28 is not connected to the current source 36 during calibration operation. The current source 36 is operable to provide a DC or an AC current. For example, the current source 36 is a transistor, amplifier or other structure for generating a waveform emulating likely waveforms received over the transmit/receive lines 16. For example, a sinusoidal waveform resulting in a voltage less than 0.7 volts positive or −0.7 volts is generated. The current passes through the switches 26 and 28 and the clipping diodes 20 to the transmit/receive lines 16. Using sequential operation, each receiver 14 is sequentially operated to measure the amplitude and phase of the received waveform. For example, the receivers 14 digitize the analog waveforms with analog-to-digital converters and measure the gain and phase using processors. A relative gain and phase of each receiver 14 as compared to other receivers 14 is used to determine an adjustment. As a result, differences in the receivers 14 are minimized or calibrated so that waveforms received at each transducer element are beamformed without artifacts introduced by the receivers 14. Any gain or phase adjustments are then applied by the apodization amplifiers and phase rotators or delays of the receivers 14 during imaging.

FIG. 5 shows one embodiment of a circuit for both transmit and receive calibration of an ultrasound system using clipping diodes. The switches 26 and 28 operate as described above, but connect to different transmit and receive calibration circuitry.

The switch 26 selectably connects between the positive high voltage source 22 and a current source 40. The current source 40 is a transistor, amplifier, integrated circuit, operational amplifier, passive components, combinations thereof or other now known or later developed current source. In one embodiment, the current source has an output impedance of about or at least 1000 Ohms and sinks about 1 mA for each transmit/receive path 16. For example, if there are thirty two transmit/receive paths 16 connected through the clipping diodes 20 to the same switches 26, 28 and/or current source 40, the current source is operable to sink 32 mA.

The switch 28 is connected to another current source 42. The current source 42 is a transistor, amplifier, integrated circuit, operational amplifier, passive components, combinations thereof or other now known or later developed current source. The current source 42 has similar impedance characteristics as discussed above for the other current source 40, but may have different impedance characteristics. The current source 42 is operable to provide a same level of current as sunk by the other current source 40, but a lesser or greater amount may be provided. The level of current provided is controlled, preset or provided as a function of the amount of current drawn.

For calibration, the switches 26 and 28 connect to the current sources 40 and 42. This connection forward biases the clipping diodes 20 and switches the clipping diodes 20 into a low impedance state. The transmit/receive paths 16 are more effectively connected to a common transmit and receive calibration node 44. For transmit calibration, the amplifier 32 and analog-to-digital converter 30 operate as described above. At a different time, receive calibration is provided by injecting signals from the current source 36 as described above.

The transmitters 12 may include one or more grass clipper diodes to electrically isolate the transmitters 12 from the transmit/receive path 16 during receive operation or receiving small electrical signals. Similarly, each receiver 14 may include a switch to isolate the receiver 14 from the transmit/receive path 16 during high voltage transmit operation. The individual transmitters 12 and receivers 14 are calibrated with a single or the common transmit and receive calibration node 44 for calibrating multiple channels in one embodiment. Alternatively, separate calibration circuitry is provided for different ones or groups of transmitters 12 and/or receivers 14. During calibration, the transducer elements are isolated from the transmit/receive paths 16. For example, any transducer is disconnected. Alternatively, switches are used to isolate the transducer elements. As yet another alternative, the system switches the transmit/receive paths 16 for calibration to connect with a transducer connector that is not currently used.

In a method for calibrating the transmit/receive path of an ultrasound system where the transmit/receive path includes clipping diodes to limit an output voltage, the clipping diodes are used as a calibration node for the transmit/receive path. Using the clipping diodes as the calibration node may avoid or minimize connection of resistors or capacitances to the transmit/receive line. The current used for calibrating in both transmit and receive passes through the clipping diodes 20. Using the clipping diodes as the calibration node may reduce the costs and circuit board area dedicated to calibration. Discontinuity on the transmission lines is avoided during normal operation, allowing for higher frequency operation in imaging. Calibration at higher frequencies is also provided without degradation of performance.

FIG. 4 shows one embodiment of a method for calibration of ultrasound transmitter and/or receivers. Additional, different or fewer acts may be provided in the same or different order. For example, an imaging mode of act 50 is implemented prior to the calibration mode of act 42.

In act 42, a calibration mode is implemented. Any dual function components are switched to a calibration function. For example, clipping diodes are disconnected from high voltage sources and connected to transmit or receive calibration circuits. Measurement and calibration are performed while the clipping diodes are disconnected from the high voltage sources. One or more clipping diodes may alternatively be connected to a voltage source while other clipping diodes are used for calibration. When the clipping diodes are not currently connected to the voltage source, the clipping diodes are disconnected from the high voltage source without further switching. The transmitters or receivers are configured for calibration, such as controlling the transmitters and receivers to operate in the sequential manner as a function of path or beamformer channel.

In act 44, a calibration signal is generated. For transmit calibration, a transmit waveform is generated on a transmit path. In response to the transmit waveform on a transmit path, a signal is generated through a clipping diode. The signal acts as a transmit calibration signal. Each of the transmitters or transmit paths sequentially generates a calibration signal and associated measurement of the signal. In one embodiment, all of the transmit paths, such as 64, 128, 196, 256 or other numbers of transmit paths are sequentially used to generate calibration signals.

For receive calibration, a signal is generated with a current source connected with the clipping diodes. The current source generates a signal on one, all or a subset of the receive paths. Each of the receivers associated with the receive path is sequentially operated to receive the generated receive calibration signal. In an alternative embodiment, groups or all of the receivers are operated substantially simultaneously to receive the generated calibration signal.

In act 46, the calibration signal is measured. For transmit calibration, a transmit calibration circuit measures the calibration signal. For receive calibration, receivers of the receive beamformer measure the calibration signal. One or both of phase and amplitude are measured. The measured calibration signal is provided through one or more clipping diodes operated as anti-parallel diodes for calibration. For each transmit/receive line, the calibration signal may be responsive to multiple clipping diodes, such as the pair of diodes connected with the transmit/receive line. The measurement is performed in one embodiment by converting the calibration signal from an analog-to-digital form. Alternatively, measurements are made on an analog waveform without conversion. A peak amplitude, a peak positive amplitude, a peak negative amplitude, and/or phase are measured. In one embodiment, the offset of the measured amplitudes and phase from the generated waveform is determined. Each of the transmitters or receivers is adjusted as a function of the offset from the source of the calibration signal. In other embodiments, the offsets are relative by comparing amplitudes and phases between different channels without comparison to the generated calibration signal.

In act 48, an ultrasound transmitter and/or receiver is calibrated as a function of the phase, amplitude or combinations thereof. For example, a phase, amplitude or both phase and amplitude characteristic of a transmit path is adjusted relative to a different transmit path. The amount of delay or phase rotation and amount of apodization is adjusted during imaging operation. As another example, the phase, amplitude or both the phase and amplitude characteristic of one received path is adjusted relative to another receive path. During imaging operation, the adjustment is implemented as a change of gain, delay or phase rotation for receiving ultrasound signals. The calibration may result in a more uniform operation as a function of channel by the transmit or receive beamformers. System induced differences are minimized.

In act 50, an imaging mode is implemented. The clipping diodes are connected with high voltages. The transmit/receive paths are then operated while the clipping diodes are connected with the high voltages. The clipping diodes and the high voltages act to limit an output voltage of an ultrasound transmitter. The output voltage is limited between positive and negative voltages connected through the pairs of clipping diodes. The connection and disconnection of the clipping diodes from the high voltage sources and the calibration circuits provides for operation in imaging and calibration modes. During the imaging mode, the transmitters 12 transmit waveforms generated as a function of calibration adjustments. For receive operations, the receivers 14 receive and process signals representing acoustic echoes as a function of calibration adjustments.

In one embodiment, each transmit/receive line 16 is associated with a single transducer element. In other embodiments, each transmit/receive line 16 is associated with two or more transducer elements. For example, the signals from two or more elements are multiplexed onto a same transmit/receive line 16. To minimize loss of information, the associated frequency of signals along the transmit/receive line 16 is increased. For the single transducer embodiment, a higher imaging frequency may be used. Regardless of the source, using the clipping diodes as a calibration node may avoid resistive or capacitive based discontinuities or degradation provided by capacitive or resistive calibration nodes for higher frequency imaging or calibration.

The calibration is performed at the place of manufacture in one embodiment. All subsequent imaging is then performed in response to the same calibration. Alternatively or additionally, the calibration is performed in response to other triggers. For example, calibration is automatically performed each time a new transducer is connected with an imaging system, every certain period of time, during routine maintenance, at the beginning of each imaging session, in response to a broadcast trigger or periodically within an imaging session. The calibration is performed while the transducer is spaced away from a patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents that are intended to define the spirit and scope of this invention.

We claim:

1. A method for calibration of an ultrasound transmitter and/or receiver, the method comprising:
   (a) measuring phase, amplitude, or both with a signal provided through a clipping diode; and
   (b) calibrating the ultrasound transmitter and/or receiver as a function of the phase, amplitude, or both.

2. The method of claim 1 further comprising:
   (c) connecting the clipping diode with a high voltage;
   (d) operating a transmit/receive path connected with the clipping diode in an imaging mode while the clipping diode is connected with the high voltage; and
   (e) disconnecting the clipping diode from the high voltage;
   wherein (a) and (b) are performed while the clipping diode is disconnected.

3. The method of claim 1 further comprising:
   (c) limiting an output voltage of the ultrasound transmitter with the clipping diode.

4. The method of claim 3 wherein (c) comprises limiting the output voltage between a positive and negative voltage with the clipping diode and an additional clipping diode, wherein (a) the phase, amplitude, or both are responsive to the signal through the clipping diode and an additional signal through the additional clipping diode.

5. The method of claim 1 further comprising:
   (c) generating a transmit waveform on a transmit path, the signal through the clipping diode responsive to the transmit waveform.

6. The method of claim 5 wherein (a) and (c) are performed sequentially for each of at least two different transmit paths, wherein (b) comprises adjusting a phase or amplitude characteristic of one of the two different transmit paths relative to the other of the two different transmit paths during imaging operation.

7. The method of claim 1 wherein (a) comprises converting the signal from analog-to-digital.

8. The method of claim 1 further comprising:
   (c) generating the signal with a current source connected with the clipping diode;
   wherein (a) comprises measuring the signal on an ultrasound receive path.

9. The method of claim 8 wherein (a) and (c) are performed sequentially for each of at least two different receive paths, wherein (b) comprises adjusting one of a phase and amplitude characteristic of one of the two different receive paths relative to the other of the two different receive paths during imaging operation.

* * * * *